(12) United States Patent
Chang et al.

(10) Patent No.: US 9,658,089 B2
(45) Date of Patent: May 23, 2017

(54) ELECTROMAGNETIC FLOWMETER WITH VOLTAGE-AMPLITUDE CONDUCTIVITY-SENSING FUNCTION FOR A LIQUID IN A TUBE

(71) Applicant: FINETEK Co., Ltd., New Taipei (TW)

(72) Inventors: Ming-Hui Chang, New Taipei (TW);
Chi-Chih Chou, New Taipei (TW);
Chun-Ju Chen, New Taipei (TW);
Chun-Hung Chen, New Taipei (TW);
Yi-Liang Hou, New Taipei (TW)

(73) Assignee: Finetek Co., Ltd., New Taipei (TW)

( * ) Notice: Subject to any disclaimer, the term of this patent is extended or adjusted under 35 U.S.C. 154(b) by 274 days.

(21) Appl. No.: 14/504,157

(22) Filed: Oct. 1, 2014

(65) Prior Publication Data
US 2016/0097662 A1 Apr. 7, 2016

(51) Int. Cl.
*G01F 1/60* (2006.01)

(52) U.S. Cl.
CPC .................................. *G01F 1/60* (2013.01)

(58) Field of Classification Search
CPC ..... G01F 1/60; G01F 1/58; G01F 1/56; G01L 1/10; G01L 1/20; G01L 1/22; G01N 17/00; G01N 27/02; G01N 27/04; G01N 27/025; G01R 27/00; G01R 27/08

USPC ................. 324/691, 713; 73/861.08, 861.11, 73/861.12, 861.16; 702/87
See application file for complete search history.

(56) References Cited

U.S. PATENT DOCUMENTS 5,677,496 A * 10/1997 Mochizuki ................ G01F 1/60
 73/601
9,285,256 B1 * 3/2016 Chang ........................ G01F 1/60

* cited by examiner

*Primary Examiner* — Tung X Nguyen
*Assistant Examiner* — Robert P Alejnikov, Jr.
(74) *Attorney, Agent, or Firm* — Muncy, Geissler, Olds & Lowe, P.C.

(57) ABSTRACT

An electromagnetic flowmeter with voltage-amplitude conductivity-sensing function for a liquid in a tube includes a first microprocessor, a transducer, flow-sensing device, an exciting-current generating device, a voltage-amplitude conductivity-sensing device, and a switch. The transducer includes coils and sensing electrodes. The switch is electrically connected to the first microprocessor and the sensing electrode. The switch is selectively connected to the flow-sensing device or the voltage-amplitude conductivity-sensing device according to the signals sent from the microprocessor. The microprocessor drives the exciting-current generating device to generate an exciting current when the switch is connected to the flow-sensing device. The microprocessor stops the exciting-current generating device from generating exciting current and computing conductivity of liquid when the switch is electrically connected to the voltage-amplitude conductivity-sensing device.

10 Claims, 6 Drawing Sheets

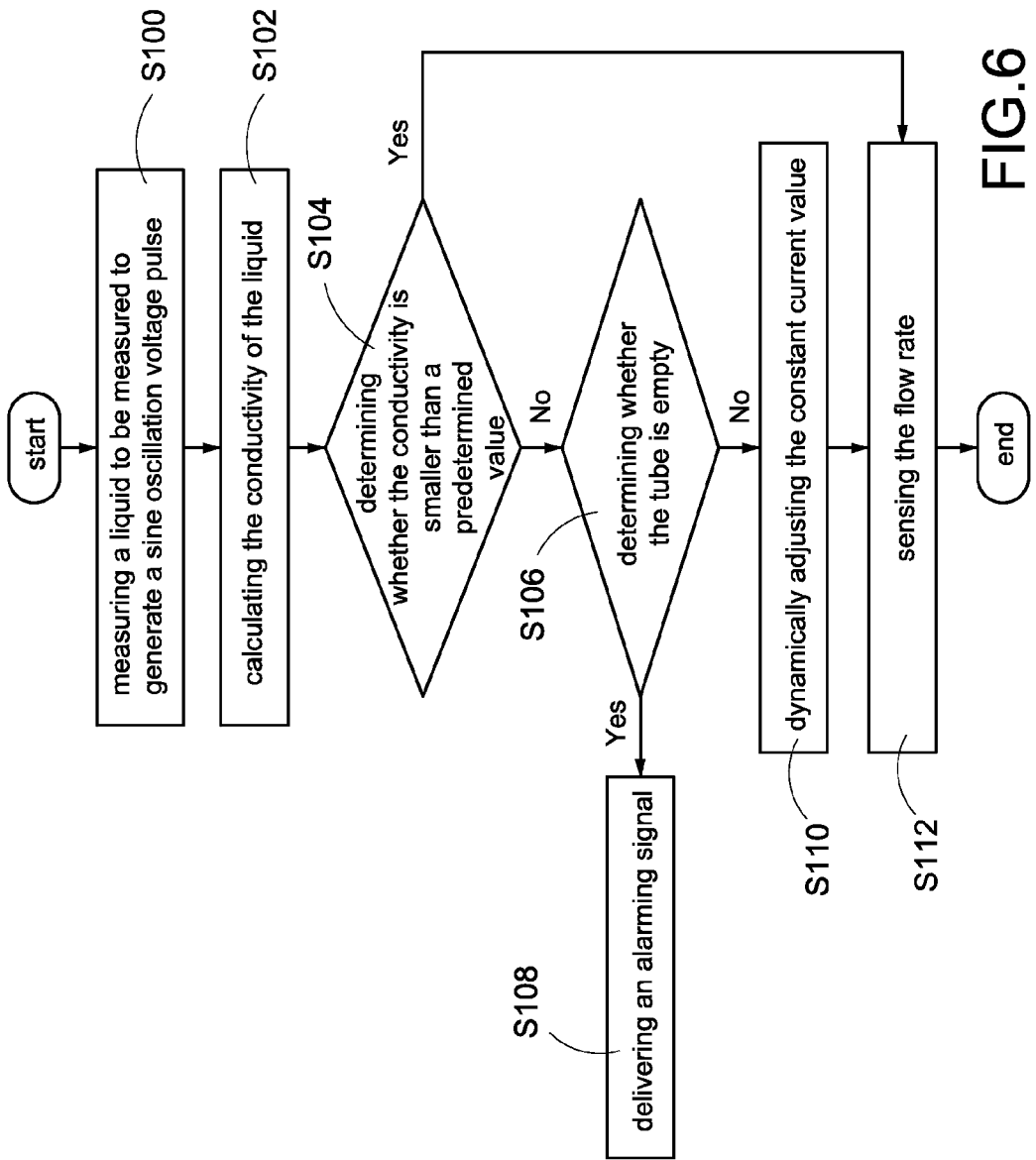

ELECTROMAGNETIC FLOWMETER WITH VOLTAGE-AMPLITUDE CONDUCTIVITY-SENSING FUNCTION FOR A LIQUID IN A TUBE

BACKGROUND OF THE INVENTION

1. Field of the Invention

The present invention relates to a flowmeter, and more particularly, to an electromagnetic flowmeter with voltage-amplitude conductivity-sensing function for a liquid in a tube.

2. Description of Related Art

Conductance refers to the ability of materials to allow currents to flow through. In a solid, the current is transmitted via electrons. In a liquid, the current is transmitted via the movement of cations and anions. Conductivity refers to the ability of materials to transmit the current. The conductivity of a liquid is relevant to the concentration of the dissolved ions. The conductivity meter is a device for measuring the ability of transmitting currents for a liquid.

Traditional conductivity meter often uses a constant current source (micro-ampere class) or a Wheatstone bridge structure for measuring. However, it tends to be influenced by the noises and ripples in circuit because output current is small. Also, the measuring range is not wide enough so that the measuring precision is not stable and not high enough.

Further, the traditional conductivity meter measures the conductivity of a liquid usually via a constant induced current. However, when the conductivity of the liquid is rather low, the induced current for measuring liquids would also decrease. It may result in difficulties when manufacturing the conductivity meter because it is hard to generate induced currents which are small.

SUMMARY OF THE INVENTION

The present invention provides an electromagnetic flowmeter with voltage-amplitude conductivity-sensing function for a liquid in a tube. The electromagnetic flowmeter is used to sense and measure the flow rate and the conductivity of a liquid.

In order to realize the above mentioned function, the electromagnetic flowmeter with voltage-amplitude conductivity-sensing function for a liquid in a tube comprises a first microprocessor, a transducer, an exciting-current generating device, a flow-sensing device, a voltage-amplitude conductivity measuring device and a switch. The transducer comprises two coils and two sensing electrodes. The exciting-current generating device is electrically connected to the first microprocessor and the coils. The flow-sensing device is electrically connected to the first microprocessor. The voltage-amplitude conductivity measuring device is electrically connected to the first microprocessor. The switch is electrically connected to the sensing electrodes, the first microprocessor, the flow-sensing device and the voltage-amplitude conductivity measuring device.

The switch makes an electrical connection between the sensing electrodes and the flow-sensing device or the sensing electrodes and the voltage-amplitude conductivity measuring device according to a signal sent by the first microprocessor. The first microprocessor is configured to drive the exciting-current generating device to generate an exciting current when the sensing electrodes and the flow-sensing device are electrically connected so as to calculate flow rate of the liquid. The first microprocessor is configured to stop the exciting-current generating device from generating the exciting current when the sensing electrodes and the voltage-amplitude conductivity measuring device are electrically connected so as to calculate conductivity of the liquid.

Moreover, the present invention provides a method for sensing conductivity and flow rate of a liquid in a tube, comprising: (a) generating a sine oscillation voltage pulse; (b) calculating a conductivity via the sine oscillation voltage pulse; (c) determining whether the conductivity is smaller than a predetermined value; (d) determining whether a tube is empty; (e) after the step (d), adjusting current value of a constant current; and (f) sensing flow rate of the liquid. The above step (b) further comprises the following steps: (b1) calculating an impedance value via the sine oscillation voltage pulse; and (b2) calculating the conductivity via the impedance value.

For further understanding of the instant disclosure, reference is made to the following detailed description illustrating the embodiments and examples of the instant disclosure. The description is only for illustrating the instant disclosure, not for limiting the scope of the claim.

BRIEF DESCRIPTION OF THE DRAWINGS

Embodiments are illustrated by way of example and not by way of limitation in the figures of the accompanying drawings, in which like references indicate similar elements and in which:

FIG. 6 is a flow chart for flow sensing and conductivity measuring of the present invention.

DETAILED DESCRIPTION OF PREFERRED EMBODIMENTS

Based on a preferred embodiment of the present invention, it is described with figures as below.

Figure 1:
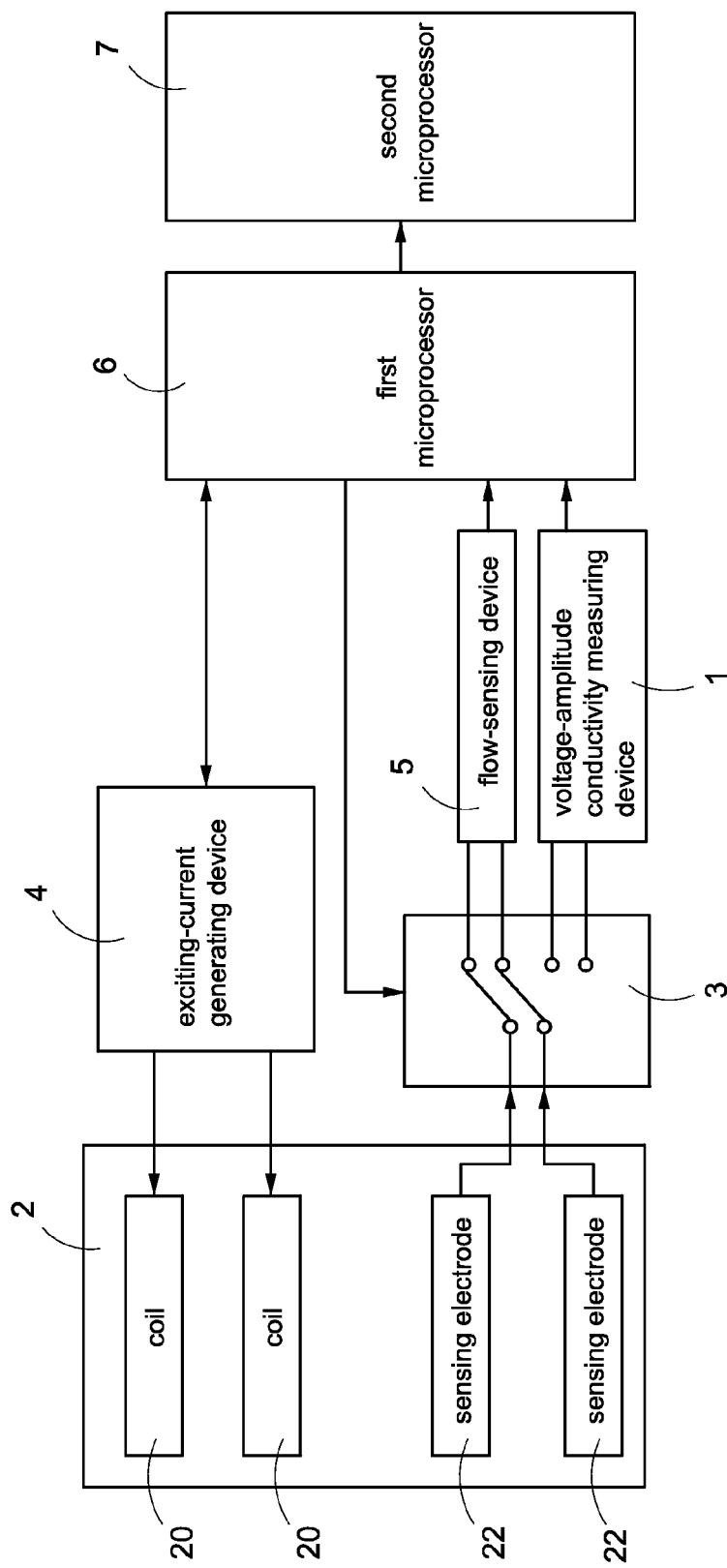
FIG. 1 is a circuit block diagram of electromagnetic flowmeter with voltage-amplitude conductivity-sensing function for a liquid in a tube of the present invention, which is operated in a first status.
Figure 2:
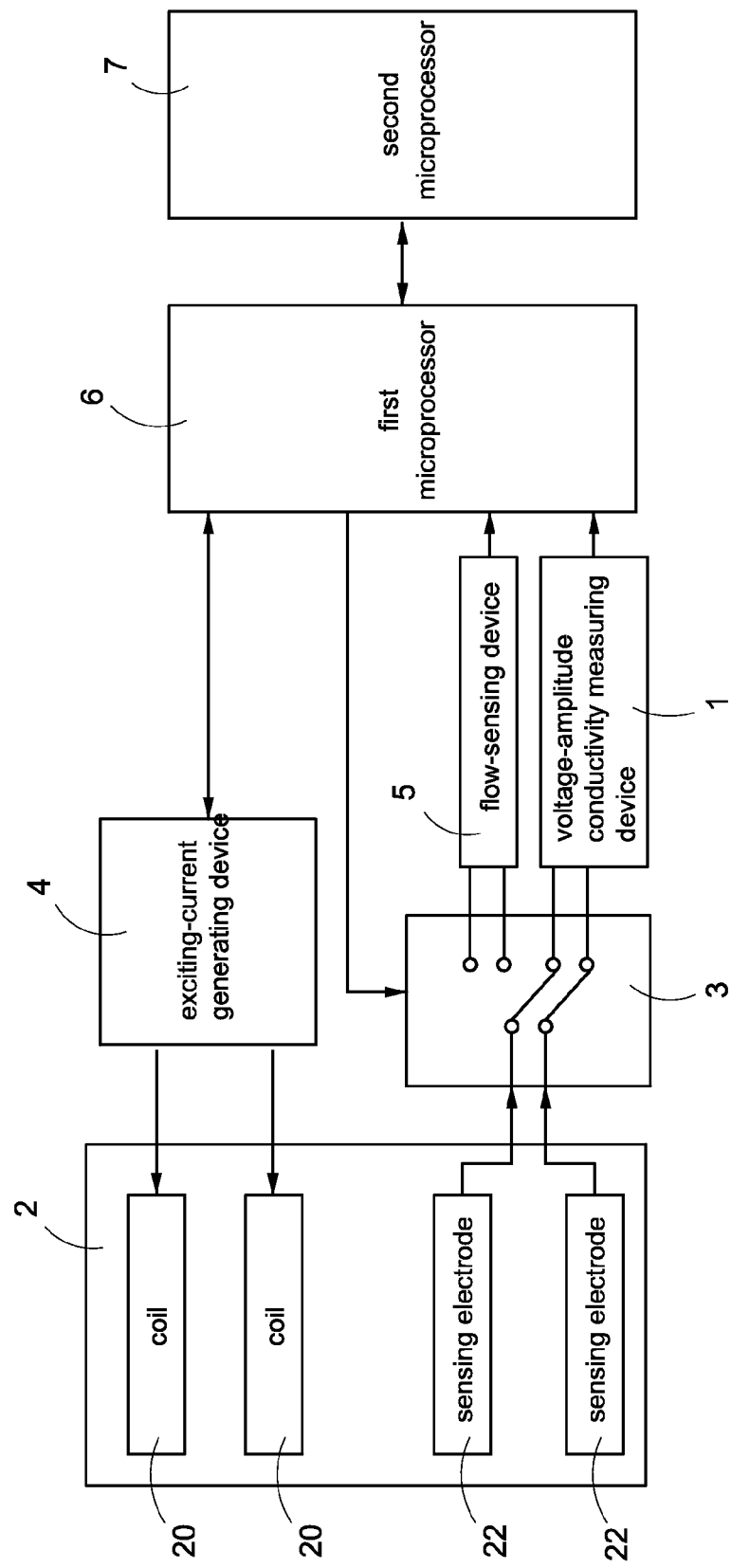
FIG. 2 is a circuit block diagram of electromagnetic flowmeter with voltage-amplitude conductivity-sensing function for a liquid in a tube of the present invention, which is operated in a second status.

In conjunction with FIG. 1 and FIG. 2, FIG. 1 and FIG. 2 are circuit block diagrams of electromagnetic flowmeter with voltage-amplitude conductivity-sensing function for a liquid in a tube according to the present invention, which are operated in a first status and a second status respectively. When operated in the first status, the electromagnetic flowmeter is used to sense the flow rate of a liquid. When operated in the second status, the electromagnetic flowmeter is used to measure the conductivity of the liquid, and to determine the wear of the sensing electrode 22 and whether the tube for transmitting the liquid to be measured is empty.

The electromagnetic flowmeter with voltage-amplitude conductivity-sensing function for a liquid in a tube comprises a voltage-amplitude conductivity measuring device 1, a transducer 2, a switch 3, an exciting-current generating device 4, a flow-sensing device 5, a first microprocessor 6 and a second microprocessor 7. The voltage-amplitude conductivity measuring device 1 is electrically connected to the switch 3 and the first microprocessor 6. The transducer 2 is electrically connected to the switch 3 and the exciting-current generating device 4. The transducer 2 comprises two coils 20 and two sensing electrodes 22. The coils 20 are electrically connected to the exciting-current generating device 4, and the sensing electrodes 22 are electrically connected to the switch 3. The sensing electrodes 22 may be made from materials such as graphite, cupper sheet, platinum or other metals, which are immerged into the liquid which is to be measured. The flow-sensing device 5 is electrically connected to the switch 3 and the first microprocessor 6. The first microprocessor 6 is electrically connected to the switch 3 and the exciting-current generating device 4. The second microprocessor 7 is electrically connected to the first microprocessor 6.

The first microprocessor 6 is configured to control the switching status of the switch 3 and the operating status of the exciting-current generating device 4, and to receive and process signals sent from the voltage-amplitude conductivity measuring device 1, the exciting-current generating device 4 and the flow-sensing device 5. The second microprocessor 7 is configured to process signals related to display, signal input and output or transmission interface. Herein, the first microprocessor 6 is configured to control and transmit the internal signals of the electromagnetic flowmeter. The second microprocessor 7 is configured to control the external communication signal transmission of the electromagnetic flowmeter. Thereby, it prevents from the interference between signals transmitted inside the electromagnetic flowmeter and signals for external communication of the electromagnetic flowmeter. Also, the signals can be efficiently distributed and used. It should be noted that, the first microprocessor 6 and the second microprocessor 7 may be electrically connected to an external communication interface so as to store or transmit data. Practically, the first microprocessor 6 and the second microprocessor 7 may be integrated into a single processor.

The switch 3 determines the operation device of the electromagnetic flowmeter according to the control signal sent by the first microprocessor 6. In the first status (as shown in FIG. 1), the switch 3 electrically connects the sensing electrode 22 and the flow-sensing device 5, and the electromagnetic flowmeter is used to sense the flow rate of the liquid which is to be measured. In the second status (as shown in FIG. 2), the switch 3 electrically connects the sensing electrode 22 and the voltage-amplitude conductivity measuring device 1, and the electromagnetic flowmeter is used to measure the conductivity of the liquid to be measured.

Figure 3:
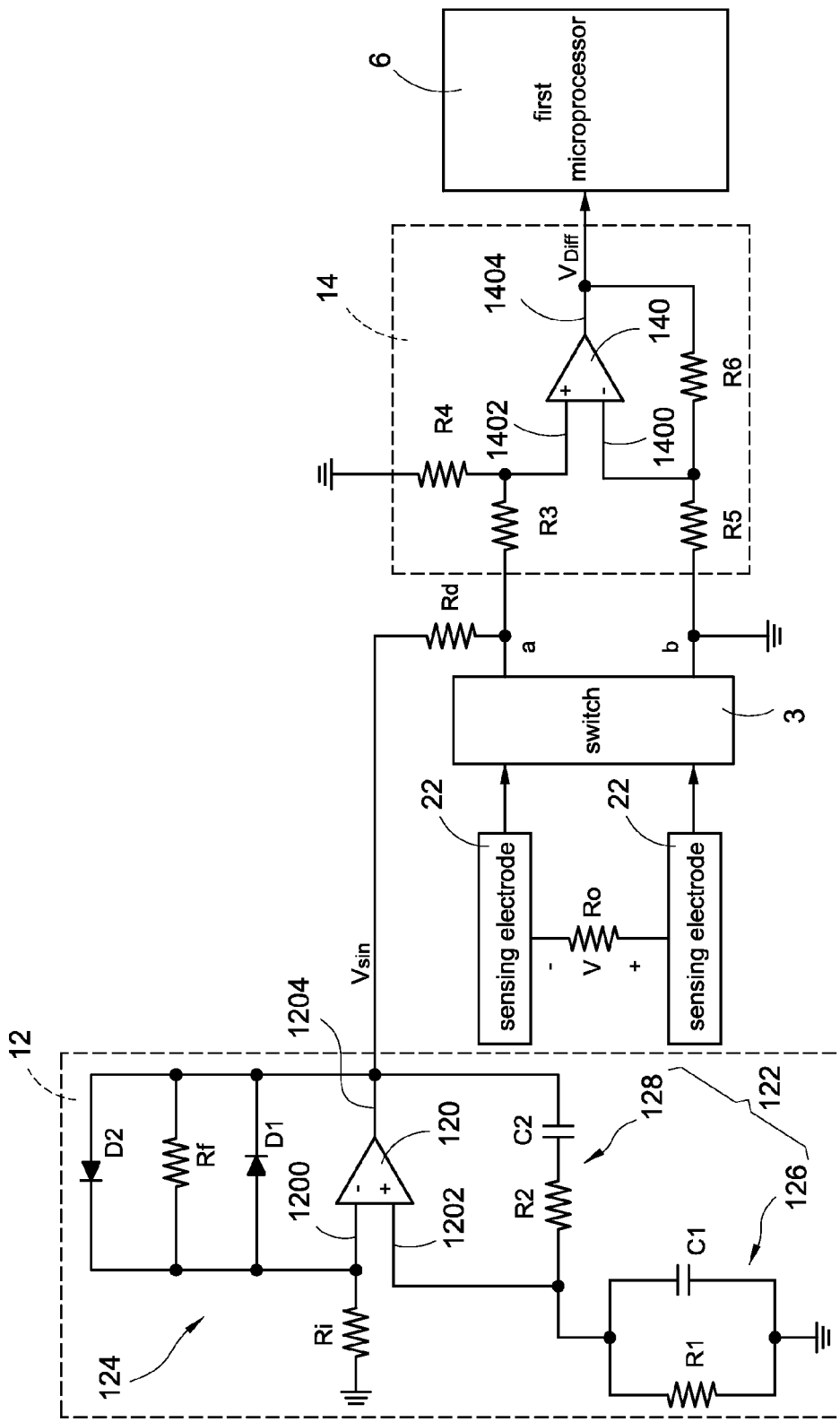
FIG. 3 is a circuit diagram of a voltage-amplitude conductivity measuring device of the present invention.

Please refer to FIG. 3, FIG. 3 is a circuit diagram of a voltage-amplitude conductivity measuring device of the present invention. The voltage-amplitude conductivity measuring device 1 comprises an oscillating module 12, a differential amplification module 14 and a voltage division resistor Rd. The first microprocessor 6 is electrically connected to the differential amplification module 14. The switch 3 is electrically connected to the differential amplification module 14 and the sensing electrode 22. The oscillating module 12 is electrically connected to the differential amplification module 14 and the switch 3 via the voltage division resistor Rd.

The oscillating module 12 comprises an operational amplifier 120, a positive feedback unit 122 and a negative feedback unit 124. The operational amplifier 120 comprises an inverting input end 1200, a non-inverting input end 1202 and an output end 1204. The negative feedback unit 124 is electrically connected to the inverting input end 1200 and the output end 1204 of the operational amplifier 120. The positive feedback unit 122 is electrically connected to the non-inverting input end 1202 and the output end 1204 of the operational amplifier 120.

The positive feedback unit 122 comprises a first resistor R1, a second resistor R2, a first capacitor C1 and a second resistor R2. One end of the first resistor R1 is electrically connected to the non-inverting input end 1202 of the operational amplifier 120, and another end of the first resistor R1 is grounded. The first capacitor C1 is electrically connected to the first resistor in parallel. That is, one end of the first capacitor C1 is electrically connected to the non-inverting input end 1202 of the operational amplifier 120, and another end of the first capacitor C1 is grounded. The first resistor R1 and the first capacitor C1 together form a RC parallel network 126.

One end of the second resistor R2 is electrically connected to the non-inverting input end of the operational amplifier 120, and another end of the second resistor R2 is electrically connected to the second capacitor C2. The end of the second capacitor C2, which is not electrically connected to the second resistor R2, is electrically connected to the output end of the operational amplifier 120. That is, the second resistor R2 and the second capacitor C2 are connected in series between the non-inverting input end 1202 and the output end 1204 of the operational amplifier 120. The second resistor R2 and the second capacitor C2 together form an RC series network 128.

The negative feedback unit 124 comprises an input resistor Ri, a feedback resistor Rf, a first diode D1 and a second diode D2. One end of the input resistor Ri is electrically connected to the inverting input end 1200 of the operational amplifier, and another end of the input resistor Ri is grounded. One end of the feedback resistor Rf is electrically connected to the inverting input end 1200 of the operational amplifier 120, and another end of the feedback resistor Rf is electrically connected to the output end 1204 of the operational amplifier 120. The operational amplifier 120, the input resistor Ri and the feedback resistor together form a non-inverting amplifier with magnifying power 1+Rf/Ri.

The anode of the first diode D1 is electrically connected to the inverting input end of the operational amplifier 120, and the cathode of the first diode D1 is electrically connected to the output end 1204 of the operational amplifier 120. The anode of the second diode D2 is electrically connected to the output end 1204 of the operational amplifier 120, and the cathode of the second diode D2 is electrically connected to the inverting input end 1200 of the operational amplifier 120. The first diode D1 and the second diode D2 are used to regulate the negative feedback so as to prevent distortion of the waveform output by the oscillating module 12. Also, the nonlinearity of the first diode D1 and the second diode D2 result in the amplitude stabilizing.

It should be noted that, the voltage-amplitude conductivity measuring device 1 determines the conductivity of the liquid to be measured via the mechanism converting voltage to impedance (see details as below). It results in errors when determining the conductivity if the voltage waveform output by the oscillating module is distorted. Thus, the first diode D1 and the second diode D2 are used to prevent from errors when determining the conductivity.

The operational amplifier 120, the positive feedback unit 122 and the negative feedback unit 124 of the oscillating module 12 oscillates and the output end 1204 of the operational amplifier 120 outputs the sinusoidal signal Vsin when the operational amplifier 120 is powered on, wherein the oscillating frequency of the sinusoidal signal Vsin is determined by the parallel network 126 and the series network 128 of the positive feedback unit. The sinusoidal signal Vsin is transmitted to the differential amplification module 14 via the voltage division resistor Rd.

The differential amplification module 14 comprises an operational amplifier 140, a third resistor R3, a fourth resistor R4, a fifth resistor R5 and a sixth resistor R6. The operational amplifier 140 comprises an inverting input end 1400, a non-inverting input end 1402 and an output end 1404, and the output end 1404 is electrically connected to the first microprocessor 6. The third resistor R3 is electrically connected to the voltage division resistor Rd and the non-inverting input end of the operational amplifier 140. The fourth resistor R4 is electrically connected to the non-inverting input end 1402 of the operational amplifier 140 and the round. One end of the fifth R5 is electrically connected to the inverting input end 1400 of the operational amplifier 140, and another end of the fifth resistor R5 is electrically connected to the switch 3 and the ground. The sixth resistor R6 is electrically connected to the inverting input end 1400 and the output end 1404 of the operational amplifier 140. Herein, the division resistor Rd and the third resistor R3 are defined as a "node a", and the fourth resistor R4 and the ground are defined as a "node b", wherein the voltage value of the node a is Va and the voltage value of the node b is Vb.

Figure 5:
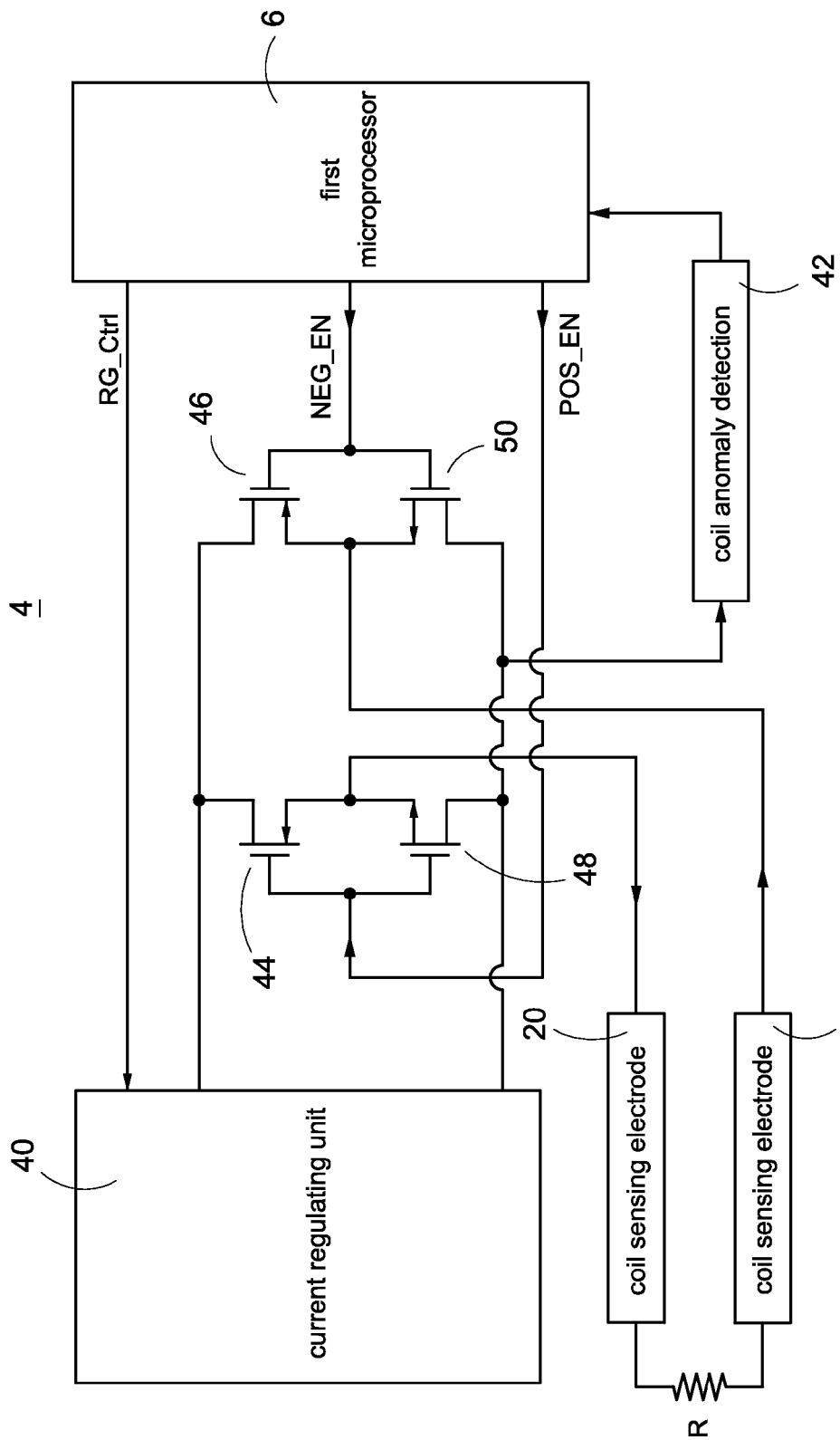
FIG. 5 is a circuit diagram of an exciting current unit of the present invention.

Please refer to FIG. 5, the exciting-current generating device 4 comprises a current regulating unit 40, a coil anomaly detection 42, a first switch element 44, a second switching element 46, the third switching element 48 and a fourth switching element 50. The first microprocessor 6 is electrically connected to the current regulating unit 40 and the coil anomaly detection 42. The detection signal output end RG_Ctrl of the first microprocessor 6 outputs a detection signal so as to dynamically adjust the constant current value output by the current regulating unit 40. Herein, the constant current refers to the current having no polarity; however, the constant current value can be adjusted by the signal output by the first microprocessor 6.

In this embodiment, the first switching element 44 and the second switching element 46 are respectively P type metal-oxide-semiconductor field-effect transistors (MOSFET). The third switching element 48 and the fourth switching element 50 are N type MOSFETs. Drain of the first switching element 44 is electrically connected to the current regulating unit 40. Gate of the first switching element 44 is electrically connected to the first signal output end POS_EN of the first microprocessor 6. Source of the first switching element 44 is electrically connected to source of the third switching element 48 and the coil 20. Drain of the second switching element 46 is electrically connected to the current regulating unit 40. Gate of the second switching element 46 is electrically connected to the second signal output end of the first microprocessor 6 and gate of the fourth switching element 50. Source of the second switching element 46 is electrically connected to source of the fourth switching element 50 and the coil 20. Drains of the third switching element 48 and the fourth switching element 50 are electrically connected to the current regulating unit 40 and the coil anomaly detection unit 42.

The current regulating unit 40 generates the constant current, which is controlled by the first microprocessor 6. The first microprocessor 6 determines whether to transmit the constant current generated by the current regulating unit 40 to the coil 20 via controlling the switching statuses of the first switching element 44, the second switching element 46, third switching element 48 and the fourth switching element 50.

When the first signal output end POS_EN and the second signal output end NEG_EN of the first microprocessor 6 outputs high potential signals or low potential signals simultaneously, the first switching element 44, the second switching element 46, third switching element 48 and the fourth switching element 50 are cut off, and the constant current generated by the current regulating unit 40 can't be transmitted to the coil 20.

When the first signal output end POS_EN outputs a low potential signal and the second signal output end NEG_EN outputs a high potential signal, the first switching element 44 and the fourth switching element 50 are turned on and the second switching element 46 and the third switching element 48 are cut off. The constant current generated by the current regulating unit is transmitted from the upper coil 20 to the lower coil 20 (as shown in FIG. 5).

When the first signal output end POS_EN outputs a high potential signal and the second signal output end NEG_EN outputs a low potential signal, the first switching element 44 and the fourth switching element 50 are cut off and the second switching element 46 and the third switching element 48 are turned on. The constant current generated by the current regulating unit 40 is transmitted from the lower coil 20 to the upper coil 20 (as shown in FIG. 5). That is, as long as the first signal output end POS_EN and the second signal output end NEG_EN respectively output signal having different potentials, the constant current generated by the current regulating unit 40 would flow through the coil 20.

Please again refers to FIG. 1, when the electromagnetic flowmeter is operated in the first status, the first microprocessor 6 delivers a control signal to control the switch 3 so as to electrically connect the sensing electrode 22 and the flow-sensing device 5. Thereby, the electromagnetic flowmeter can sense the flow rate of the liquid to be measured. Also, the first microprocessor 6 delivers a control signal to the exciting-current generating device 4 so as to drive the exciting-current generating device 4 to generate the exciting current.

In particular, the method of transmitting the constant current generated by the current regulating unit 40 to the coil 20 comprises: 1) The first signal output end POS_EN of the first microprocessor 6 outputs a high potential signal and the second signal output end NEG_EN of the first microprocessor 6 outputs a low potential signal respectively. Thereby, the first switching element 44 and the fourth switching element 50 are turned on, and the constant current generated by the current regulating unit 40 can be transmitted to the coil 20. 2) The first signal output end POS_EN of the first microprocessor 6 outputs a low potential signal and the second signal output end NEG_EN of the first microprocessor 6 outputs a high potential signal respectively. Thereby, the second switching element 46 and the third switching element 48 are turned, and the constant current generated by the current regulating unit 40 can be transmitted to the coil 20.

The first microprocessor 6 makes the current transmitted to the coil 20 be a constant current pulse signal having a predetermined frequency via the signals output by the first output signal output end POS_EN and the second signal output end NEG_EN. The constant current pulse signal and the coil 20 generate an exciting magnetic field, wherein there is a larger exciting magnetic field generated when the current value is larger. Based on the Faraday's Law, when the conductor moves and across the magnetic field lines, there would be induced electromotive force generated at two ends of the sensing electrode 22. After the induced electromotive force is filtered (removing noises) and magnified, and has a signal conversion (converting the analog signals to the digital signals) via the flow-sensing device, it would be transmitted to the first microprocessor 6. Because the induced electromotive force is directly proportional to the flow rate of the liquid to be measured, the first microprocessor 6 uses the mechanism converting voltage to flow rate so as to calculate the flow rate of the liquid.

The coil anomaly detection 42 is used to determine whether the coil is abnormal. For example, the coil anomaly detection 42 may be a comparator, but it's not limited thereto, which is used to detect the current value. If the current flowing through the coil anomaly detection 42 is smaller than an initial predetermined value, the coil anomaly detection 42 would send a high potential signal to the first microprocessor 6 and drive the electromagnetic flowmeter to deliver an alarming signal.

Please refer to FIG. 2 again, when the electromagnetic flowmeter is operated in the second status, the first microprocessor 6 controls the switch 3 to electrically connect the sensing electrode 22 and the voltage-amplitude conductivity measuring device 1 so as to measure the conductivity of the liquid to be measured. Also, the first signal output end POS_EN and the second signal output end NEG_EN of the first microprocessor 6 simultaneously outputs high potential signals or low potential signals so as to cut off the first switching element 44, the second switching element 46, the third switching element 48 and the four switching element 50 at the same time. Thus, the constant current generated by the current regulating unit can't be transmitted to the coil 20. That is, when the electromagnetic flowmeter is operated in the second status, there is no exciting magnetic field generated.

When the electromagnetic flowmeter is operated in the second status, the electromagnetic flowmeter can be not only used for measuring the conductivity of the liquid to be measured but also used for determining the wear of the sensing electrode and whether the tube for transmitting the liquid to be measured is empty.

When the sensing electrode 22 is placed into the liquid to be measured, there is inductive impedance Ro generated between the sensing electrode 22 and the liquid, and the inductive impedance Ro may vary based on different liquids.

When the electromagnetic flowmeter is operated in the second status, the sinusoidal signal Vsin generated by the oscillating module 12 is transmitted to the differential amplification module 14 after being divided by the voltage division resistor Rd and the inductive impedance Ro. Particularly, the voltage transmitted to the differential amplification module 14 is the voltage of sinusoidal signal Vsin across two ends of the inductive impedance Ro. Moreover, the value of voltage transmitted to the differential amplification module 14 equals to the voltage difference between voltages of the sinusoidal signals at the node a and the node b, that is, $Va-Vb=(Ro/Ro+R3) \cdot Vsin$.

The voltage transmitted to the differential amplification module 14 has a signal amplification via the differential amplification module 14 and then is output from the output end 1404 of the operational amplifier 140, wherein the signal output from the output end 1404 of the operational amplifier 140 is a half-sine wave signal VDiff with voltage $VDiff=Va \cdot (1+R6/R5) \cdot [R3/(R3+R4)] - V2 \cdot (R6/R5)$.

Figure 4:
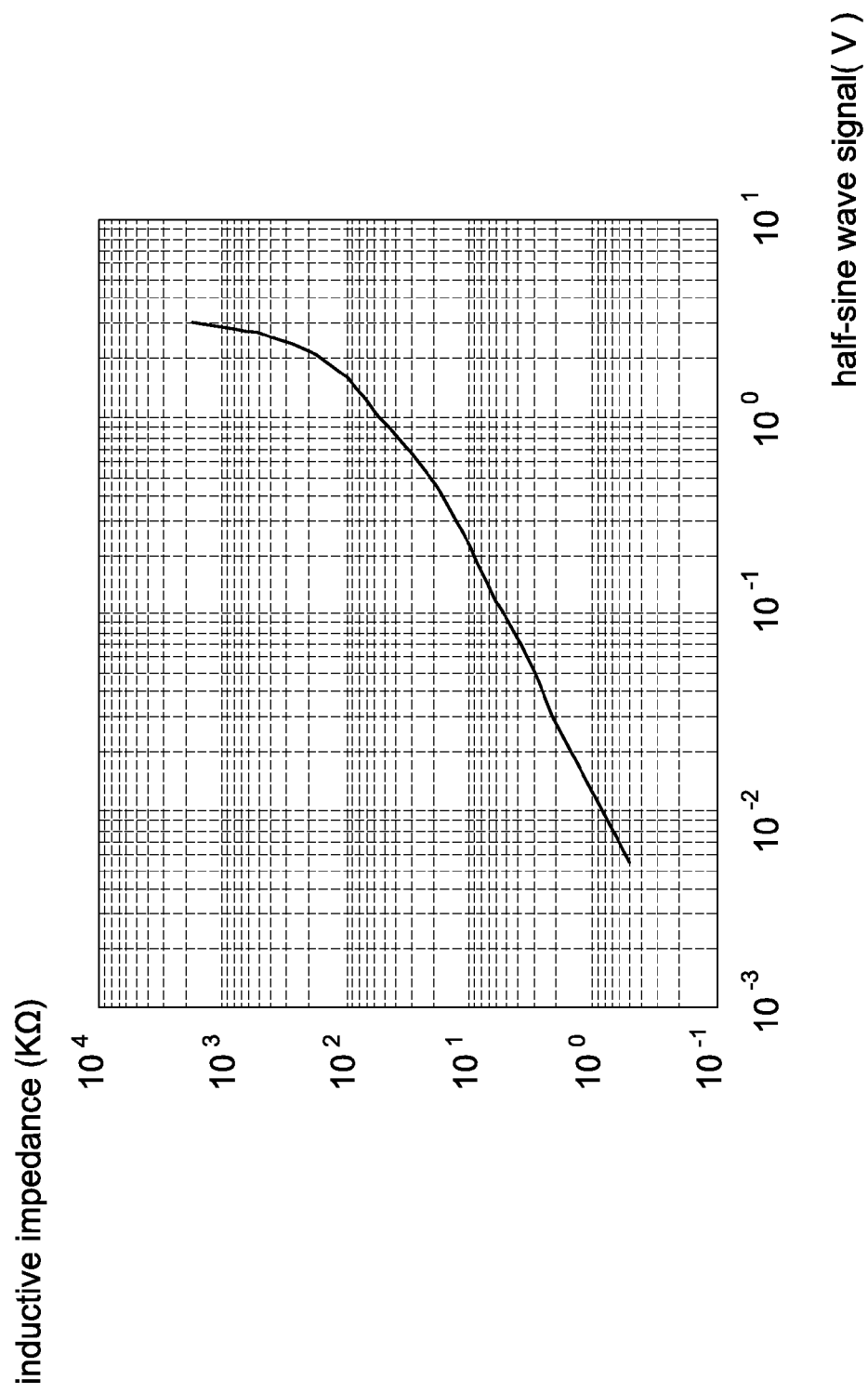
FIG. 4 is a relationship diagram of the half sine wave voltage with respect to the inductive impedance.

The half-sine wave signal VDiff output by the differential amplification module 14 is transmitted to the first microprocessor 6, the first microprocessor 6 obtains the value of inductive impedance Ro via the peak voltage of the half-sine wave signal VDiff and the relationship between the half-sine wave signal and the inductive impedance shown in FIG. 4. Finally, the microprocessor 6 obtains the conductivity of the liquid to be measured via the calculation with the equation for the conductivity of the inductive impedance Ro, which is $\sigma = d/(Ro \cdot A)$, wherein d is the distance between the sensing electrodes 22 and A is the contact area between the electrodes 22 and the liquid.

From the above, after the voltage-amplitude conductivity measuring device 1 of the present invention is powered on, the oscillating module 12 generates a sinusoidal signal Vsin. The sinusoidal signal Vsin is transmitted to the sensing electrode 22 and the liquid to be measured via the voltage division resistor Rd. The differential amplification module 14 converts the voltage of the sinusoidal signal Vsin across the sensing electrode 22 and the liquid to be measured into a half-sine wave signal VDiff, and the half-sine wave signal VDiff is then transmitted to the first microprocessor 6. The first microprocessor 6 determines the impedance of liquid to be measured via the mechanism converting voltage into impedance, and determines the conductivity of liquid to be measured via the mechanism converting impedance into conductivity.

Besides, the voltage-amplitude conductivity measuring device 1 of the present invention also can determine the wear of the sensing electrode and whether the tube for transmitting the liquid to be measured is empty. When there is certain liquid transmitted through the tube, the half-sine wave signal VDiff transmitted to the first microprocessor 6 should be a constant value. However, if the voltage value of the half-sine wave signal VDiff changes, after receiving the half-sine wave signal VDiff, the first microprocessor 6 can determine the wear of the sensing electrode and whether the tube for transmitting the liquid to be measured is empty via the mechanism converting voltage into impedance.

Please refer to FIG. 6, FIG. 6 is a flowchart for flow-sensing and conductivity measuring of the present invention. To begin with, the electromagnetic flowmeter measures the conductivity of the liquid to be measured so as to determine whether the tube for transmitting the liquid to be measured is empty. If the tube for transmitting the liquid to be measured is not empty, the electromagnetic flowmeter starts to sense the flow rate of the liquid.

The method for sensing conductivity and flow rate of a liquid in a tube comprises steps as follows: First, the electromagnetic flowmeter is operated in a second status (that is, the sensing electrodes 22 and the voltage-amplitude conductivity measuring device 1 are electrically connected), and the first microprocessor 6 receives a sinusoidal oscillating voltage pulse generated by the voltage-amplitude conductivity measuring device 1 (Step S100). The first microprocessor 6, via the above sinusoidal oscillating voltage pulse, calculates the impedance with the mechanism converting voltage into impedance, and calculates the conductivity with the mechanism converting impedance into conductivity (Step S102).

After that, the first microprocessor 6 determines whether the above conductivity is low (Step S104). If the above conductivity is low, the first microprocessor 6 further determines whether the tube for transmitting the liquid to be measured is empty (Step S106). After the Step S104, if the conductivity is not larger than a predetermined value, it starts to calculate the flow rate of the liquid to be measured (Step S112). If the first microprocessor 6 determines that the tube for transmitting the liquid to be measured is empty via the above conductivity, there is an alarming signal delivered (Step S108).

If the first microprocessor 6 determines that the tube for transmitting the liquid to be measured is not empty via the above conductivity, it means that the conductivity is low in this status so that the electromagnetic flowmeter is operated in the first status (that is, the electrodes 22 and the flow-sensing device 5 are electrically connected). After that, a detection signal output from the detection signal output end RG_Ctrl of the first microprocessor 6 is used to dynamically adjust the value of constant current output by the current regulating unit 40 (Step S110). It should be noted that, the conductivity of the liquid to be measured is considered a low one, so the detection signal delivered by the first microprocessor 6 is used to elevate the value of current output by the current regulating unit 40. At the same time, the first microprocessor 6 switches the first switching element 44, the second switching element 46, the third switching element 48 and the fourth switching element 50 so as to generate the induced electromotive force between two ends of the sensing electrode 22. The induced electromotive force is filtered, magnified and converted by the flow-sensing device 5 and then is transmitted back to the first microprocessor 6. Then, the first microprocessor 6 calculates the flow rate of the liquid via the mechanism converting voltage into flow rate (Step S112).

It should be understood that the exemplary embodiments described therein should be considered in a descriptive sense only and not for purposes of limitation. Descriptions of features or aspects within each embodiment should typically be considered as available for other similar features or aspects in other embodiments. While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. An electromagnetic flowmeter with voltage-amplitude conductivity-sensing function for a liquid in a tube, comprising:
    a first microprocessor;
    a transducer, comprising two coils and two sensing electrodes;
    an exciting-current generating device, electrically connected to the first microprocessor and the coils;
    a flow-sensing device, electrically connected to the first microprocessor;
    a voltage-amplitude conductivity measuring device, electrically connected to the first microprocessor; and
    a switch, electrically connected to the sensing electrodes, the first microprocessor, the flow-sensing device, and the voltage-amplitude conductivity measuring device;
    wherein the switch makes an electrical connection between the sensing electrodes and the flow-sensing device or the sensing electrodes and the voltage-amplitude conductivity measuring device according to a signal sent by the first microprocessor, the first microprocessor is configured to drive the exciting-current generating device to generate an exciting current when the sensing electrodes and the flow-sensing device are electrically connected so as to calculate flow rate of the liquid, and the first microprocessor is configured to stop the exciting-current generating device from generating the exciting current when the sensing electrodes and the voltage-amplitude conductivity measuring device are electrically connected so as to calculate conductivity of the liquid.

2. The electromagnetic flowmeter with voltage-amplitude conductivity-sensing function for a liquid in a tube of claim 1, wherein the voltage-amplitude conductivity measuring device comprises:
    a differential amplification module, electrically connected to the first microprocessor and the sensing electrodes;
    a voltage division resistor, electrically connected to the differential amplification module and the sensing electrodes; and
    an oscillating module, electrically connected to the voltage division resistor and configured to generate a sinusoidal signal;
    wherein the sensing electrodes are immerged in the liquid, the sensing electrodes and the liquid generate an inductive impedance together, the differential amplification module outputs a sinusoidal signal divided by the inductive impedance and the voltage division resistor and outputs a half-sine wave signal to the first microprocessor, and the first microprocessor calculates the conductivity of the liquid.

3. The electromagnetic flowmeter with voltage-amplitude conductivity-sensing function for a liquid in a tube of claim 2, wherein the oscillating module comprises an operational amplifier, a positive feedback unit and a negative feedback unit, the operational amplifier comprises an inverting input end, a non-inverting input end and an output end, the positive feedback unit is electrically connected to the non-inverting input end and the output end, the negative feedback unit is electrically connected to the inverting input end and the output end.

4. The electromagnetic flowmeter with voltage-amplitude conductivity-sensing function for a liquid in a tube of claim 3, wherein the positive feedback unit comprises a RC parallel network and a RC series network, and the RC parallel network is electrically connected to the non-inverting input end of the operational amplifier, and the series network is electrically connected to the non-inverting input end and the output end of the operational amplifier.

5. The electromagnetic flowmeter with voltage-amplitude conductivity-sensing function for a liquid in a tube of claim 4, wherein the RC parallel network comprises a first resistor and a first capacitor, one end of the first resistor is electrically connected to the non-inverting output end, another end of the first resistor is electrically connected to the ground, the first capacitor and the first resistor are connected in parallel, the RC series network comprises a second resistor and a second capacitor, one end of the second resistor is electrically connected to the non-inverting input end of the operational amplifier, another end of the second resistor is electrically connected to one end of the second capacitor, and another end of the second capacitor is electrically connected to the output end of the operational amplifier.

6. The electromagnetic flowmeter with voltage-amplitude conductivity-sensing function for a liquid in a tube of claim 5, wherein the negative feedback unit comprises an input resistor and a feedback resistor, the input resistor is electrically connected to the inverting input end of the operational amplifier and the ground, and the feedback resistor is electrically connected to the inverting input end and the output end of the operational amplifier.

7. The electromagnetic flowmeter with voltage-amplitude conductivity-sensing function for a liquid in a tube of claim 6, wherein the negative feedback unit further comprises a first diode and a second diode, anode of the first diode is electrically connected to the inverting input end of the operational amplifier, cathode of the first diode is electrically connected to the output end of the operational amplifier, anode of the second diode is electrically connected to the output end of the operational amplifier, and cathode of the second diode is electrically connected to the inverting input end of the operational amplifier.

8. The electromagnetic flowmeter with voltage-amplitude conductivity-sensing function for a liquid in a tube of claim 2, wherein the differential amplification module comprises an operational amplifier, a third resistor, a fourth resistor, a fifth resistor and a sixth resistor, the operational amplifier comprises an inverting input end, a non-inverting input end and an output end, the third resistor is electrically connected to the non-inverting input end of the operational amplifier and the voltage division resistor, the fourth resistor is electrically connected to the non-inverting input end of the operational amplifier and the ground, the fifth resistor is electrically connected to the inverting input end of the operational amplifier, the sensing electrode and the ground, and the sixth resistor is electrically connected to the inverting input end and the output end of the operational amplifier.

9. The electromagnetic flowmeter with voltage-amplitude conductivity-sensing function for a liquid in a tube of claim 1, wherein the exciting-current generating device comprises a current regulating unit, a first switching element, a second switching element, a third switching element and a fourth switching element, the current regulating unit is electrically connected to the first microprocessor, the first switching unit, the second switching unit, the third switching unit and the fourth switching unit.

10. The electromagnetic flowmeter with voltage-amplitude conductivity-sensing function for a liquid in a tube of claim 9, wherein the exciting-current generating device further comprises a coil anomaly detection, and the coil anomaly detection is electrically connected to the first microprocessor, the current regulating unit, the third switching unit and the fourth switch unit.

* * * * *